United States Patent
Grosch et al.

(10) Patent No.: US 6,518,441 B2
(45) Date of Patent: *Feb. 11, 2003

(54) METHOD FOR OXIDIZING AN ORGANIC COMPOUND CONTAINING AT LEAST ONE C-C DOUBLE BOND

(75) Inventors: Georg Heinrich Grosch, Bad Dürkheim (DE); Ulrich Müller, Neustadt (DE); Andreas Walch, Heidelberg (DE); Norbert Rieber, Mannheim (DE); Martin Fischer, Ludwigshafen (DE); Stefan Quaiser, Limburgerhof (DE); Wolfgang Harder, Weinheim (DE); Karsten Eller, Ludwigshafen (DE); Peter Bassler, Viernheim (DE); Anne Wenzel, Graben-Neudorf (DE); Gerd Kaibel, Lampertheim (DE); Achim Stammer, Freinsheim (DE); Jochem Henkelmann, Mannheim (DE); Arnd Böttcher, Frankenthal (DE); Joaquim Henrique Teles, Altrip (DE); Michael Schulz, Ludwigshafen (DE); Gert Treiber, Worms (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/424,847
(22) PCT Filed: Jun. 5, 1998
(86) PCT No.: PCT/EP98/03395
§ 371 (c)(1), (2), (4) Date: Dec. 6, 1999
(87) PCT Pub. No.: WO98/55430
PCT Pub. Date: Dec. 10, 1998

(65) Prior Publication Data
US 2002/0120158 A1 Aug. 29, 2002

(30) Foreign Application Priority Data
Jun. 6, 1997 (DE) .................................. 197 23 950

(51) Int. Cl.$^7$ .................. C07D 301/12; B01J 20/34
(52) U.S. Cl. ............................. 549/531; 502/56
(58) Field of Search ............................. 549/531; 502/56

(56) References Cited

U.S. PATENT DOCUMENTS

| | | | |
|---|---|---|---|
| 5,374,747 A | 12/1994 | Saxton et al. | |
| 5,384,418 A | 1/1995 | Zajacek et al. | |
| 5,463,090 A | 10/1995 | Rodriguez et al. | |
| 5,599,955 A | 2/1997 | Vora et al. | |
| 5,599,956 A | 2/1997 | Pujado et al. | |
| 5,741,749 A | * 4/1998 | Crocco et al. | 502/56 |
| 5,859,265 A | 1/1999 | Mueller et al. | |

FOREIGN PATENT DOCUMENTS

| | | |
|---|---|---|
| DE | 44 25 672 | 1/1996 |
| EP | 0 230 949 | 8/1987 |
| EP | 0 743 094 | 11/1996 |

OTHER PUBLICATIONS

Derwent Abstracts, AN 91–188532/26, JP 3–114536, May 15, 1991.

M.G. Clerici, et al., Journal of Catalysis, vol. 129, pps. 159–167, "Synthesis Of Propylene Oxide From Propylene and Hydrogen Peroxide Catalyzed by Titanium Silcalite", 1991.

* cited by examiner

Primary Examiner—Jafar Parsa
(74) Attorney, Agent, or Firm—Oblon, Spivak, McClelland, Maier & Neustadt, P.C.

(57) ABSTRACT

A process for oxidizing an organic compound having at least one C—C double bond or a mixture of two or more thereof comprises the following steps:

(I) preparing a hydroperoxide, (II) reacting an organic compound having at least one C—C double bond or a mixture of two or more thereof with the hydroperoxide prepared in step (I) in the presence of a zeolite catalyst, (III) regenerating the at least partially deactivated zeolite catalyst used in step (II), and (IV) conducting the reaction of step (II) using a zeolite catalyst containing the catalyst regenerated in step (III).

11 Claims, No Drawings

METHOD FOR OXIDIZING AN ORGANIC COMPOUND CONTAINING AT LEAST ONE C-C DOUBLE BOND

This application is a 371 of PCT/EP98/03395 Jun. 5, 1998.

The present invention relates to a process for oxidizing an organic compound having at least one C—C double bond or a mixture of two or more thereof by reacting the organic compound having at least one C—C double bond or the mixture of two or more thereof with a hydroperoxide in the presence of a zeolite catalyst, regenerating this catalyst, and reusing the catalyst for the above-mentioned reaction following its regeneration.

Processes for oxidizing an organic compound having at least one C—C double bond, especially olefins, preferably propylene, using a hydroperoxide are known.

U.S. Pat. No. 5,374,747 discloses such an epoxidation process using a titanium-containing molecular sieve having a structure which is isomorphous to zeolite β, and the preparation of such a molecular sieve.

U.S. Pat. No. 5,384,418 discloses an integrated process for preparing epoxides by reacting a hydroperoxide with an ethylenically unsaturated compound in the presence of a titanium silicalite.

Other processes for preparing epoxides in the presence of zeolite catalysts are disclosed, inter alia, in U.S. Pat. No. 5,463,090 and EP-A-0 230 949, the first of which produces the hydrogen peroxide used for oxidizing from an anthraquinone process, whereas the latter discloses the epoxidation of propylene with hydrogen peroxide in the presence of titanium silicalites defined therein.

According to U.S. Pat. No. 5,599,955, propylene, which is most commonly used for such oxidations, can be obtained starting from synthesis gas. U.S. Pat. No. 5,599,956 discloses a process for preparing propylene oxide, wherein the propylene is obtained by steam cracking, catalytic cracking or catalytic dehydrogenation.

It is known that in these catalytic reactions organic deposits are formed after some time, which result in partial or complete deactivation of the catalysts, especially when using catalysts having micropores, for example zeolite catalysts such as titanium silicalite or titanium-containing zeolite β.

These organic deposits can be mostly removed by calcining the catalyst or washing with solvent (M. G. Clerici, G. Bellussi, U. Romano, J. Catal., 129 (1991), 159–167; JP-A-03 114 536).

EP-A-0 743 094 discloses a process for regenerating a Ti-containing molecular sieve by heating the molecular sieve at from more than 150° C. to less than 400° C. This reference also discloses that it is possible to use the catalyst regenerated in this manner for reacting organic compounds, for example for the hydroxylation of aromatic compounds, the ammoxidation of ketones, the oxidation of saturated hydrocarbons to obtain alcohols and ketones, and for olefin epoxidation. DE-A-44 25 672 discloses an oxidation catalyst based on titanium or vanadium silicates having a zeolite structure and a process for preparing epoxides from olefins, hydrogen and oxygen using the catalyst described therein. It is also stated that the catalyst described therein may be regenerated.

Above-discussed U.S. Pat. No. 5,599,955 also mentions the possible regeneration of the catalyst used in connection with the process described therein, but no details of the regeneration procedure are given.

As can be seen from the above, there is extensive prior art relating to integrated processes for preparing epoxides, but the problem of practicable regeneration of the deactivated catalyst and the useful integration of such a step into the overall process remains unsolved. This step and its integration into the overall process are, however, critical for the economic viability of such a process. It is in principle possible to conduct regenerations as disclosed in EP-A-0 743 094; these are, however, economically unviable because of the low temperatures used therein and the resulting long regeneration period.

It is an object of the present invention to provide a process for oxidizing an organic compound having at least one C—C double bond, regenerating the catalyst used in this process and reusing the regenerated catalyst for further reaction in the process.

We have found that this object is achieved by the process of the invention.

The present invention accordingly provides a process for oxidizing an organic compound having at least one C—C double bond or a mixture of two or more thereof, which comprises the following steps:

(I) preparing a hydroperoxide,
(II) reacting an organic compound having at least one C—C double bond or a mixture of two or more thereof with the hydroperoxide prepared in step (I) in the presence of a zeolite catalyst,
(III) regenerating the at least partially deactivated zeolite catalyst used in step (II), and
(IV) conducting the reaction of step (II) using a zeolite catalyst comprising the catalyst regenerated in step (III).

Step (I)

This step relates to the preparation of a hydroperoxide. For the purposes of the present invention, hydroperoxide refers to hydrogen peroxide as well as organic compounds of the formula R—O—OH, where R is alkyl, cycloalkyl, aralkyl or aryl.

In the process of the invention, preference is given to using hydrogen peroxide.

Processes for preparing the hydroperoxides are known and will herein only be recited briefly for the synthesis of hydrogen peroxide.

Hydrogen peroxide is preferably synthesized via an anthraquinone process or directly from hydrogen and oxygen over noble metal catalysts.

In the anthraquinone process, a mixture is prepared which is referred to as working solution hereinafter. This mixture comprises a solution of a 2-alkylanthraquinone, preferably 2-ethyl-, 2-butyl-, 2-hexyl-, 2-hexenyl-, particularly preferably 2-ethylanthraquinone, in a solvent mixture comprising a quinone solvent and a hydroquinone solvent. The quinone solvent is generally selected from the group consisting of aromatic and alkylaromatic solvents, preferably benzene, toluene, xylenes or higher alkylaromatics having 6 to 20, preferably 9 to 11, carbon atoms or mixtures of two or more thereof, such mixtures being preferred.

The hydroquinone solvent is generally selected from the group consisting of alkyl phosphates, alkyl phosphonates, nonyl alcohols, alkylcyclohexanol esters, N,N-dialkylcarbonylamides, tetraalkylurethanes or N-alkyl-2-pyrrolidone and mixtures of two or more thereof, tetrabutylurea being preferred.

The working solution is hydrogenated with hydrogen at from about 20 to 100° C., preferably at from about 40 to 70° C., over a commercially available catalyst containing at least one transition metal, preferably from 0.5 to 20% by weight Pd on carbon, more preferably from 2 to 15% by weight Pd on carbon. The catalyst can be arranged in the form of a suspension or a fixed bed.

The resulting hydroquinone-containing solution is oxidized with oxygen, preferably with air, more preferably with an oxygen- and nitrogen-containing mixture in which the oxygen is present in deficiency, based on the total mixture, in a suitable apparatus, for example a bubble column. The oxidation is carried out at a reaction temperature of from about 20 to about 100° C., preferably from about 35 to about 60° C., until the hydrogen peroxide content of the solution is constant and the conversion of the hydroquinone into quinone is complete.

The resulting hydrogen peroxide mixture is subsequently extracted with a solvent which is not miscible with the solvent mixture, preferably with water, methanol, a monohydric alcohol having from 2 to 6 carbon atoms or a mixture of two or more thereof, more preferably with water. The resulting hydrogen peroxide mixture may then be used directly in the reaction of step (II) of the process of the invention. Such a work-up procedure is disclosed, inter alia, in EP-B-0 549 013, which suggests using a mixture of water and an alcohol, preferably methanol.

Furthermore, the hydrogen peroxide preferably used for oxidation in the present invention may also be prepared directly from the elements. Processes for preparing hydrogen peroxide from the elements oxygen and hydrogen are well known, as can be seen from DE-A-196 42 770 and the prior art cited therein. In the process of the invention, hydrogen peroxide is preferably prepared from the elements according to the process described in DE-A-196 42 770, which is incorporated herein by reference in its entirety.

The essential aspects of the process described therein will now be recited briefly below.

According to the process described therein, hydrogen peroxide is prepared continuously by reacting hydrogen and oxygen in water and/or $C_1$–$C_3$-alkanols as reaction medium over a shaped catalyst body containing palladium as the active component. This process yields a hydrogen peroxide solution having a hydrogen peroxide content of at least 2.5% by weight, based on the total solution.

Shaped catalyst bodies are catalysts in which the catalytically active component is on the surface of specifically shaped carriers. Such carriers can be customary packing elements, for example Raschig rings, saddle bodies, Pall® rings, wire spirals or wire-mesh rings, which are composed of various materials suitable for coating with the active component. Details of the above-mentioned carriers can be found in Römpp-Chemie-Lexikon, 9th ed., p. 1453f The packing elements provided with the catalytically active component are introduced into the reactor in the form of a loose bed. Preferred shaped bodies have channels with hydraulic radii (as defined in VDI-Wärmeatlas, chapter LE1) in the range from 1 to 10 mm.

Preference is given to using shaped catalyst bodies which are installed in the reactor in the form of arranged packings and which have a large surface area for their volume, due to a multiplicity of throughflow channels. Such shaped bodies are known as catalyst monoliths. Suitable reactors for the preparation of hydrogen peroxide according to this process are described, for example, in EP-A-0 068 862, EP-A-0 201 614 and EP-A-0 448 884.

A further process for preparing hydrogen peroxide, which can also be integrated into the process of the invention as step (I), is disclosed in WO 96/05138. This application is incorporated herein by reference in its entirety for the process for preparing hydrogen peroxide described therein and for the apparatus used for this purpose.

The process described therein involves introducing small bubbles of hydrogen and oxygen into a liquid stream of water and an inorganic acid in the presence of a catalyst comprising a metal of transition group VIII of the Periodic Table. The liquid stream has a velocity of at least about 3 m/s (10 feet/s) to create a continuous region of finely dispersed gas bubbles in a continuous liquid phase. As regards further details of this process for preparing hydrogen peroxide, reference is made to the above-mentioned document.

The hydrogen peroxide used in the process of the invention can also be prepared by contacting a secondary alcohol, for example α-methylbenzyl alcohol, isopropanol, 1-butanol or cyclohexanol with molecular oxygen under conditions suitable for obtaining a mixture comprising a secondary alcohol and hydrogen peroxide and/or a hydrogen peroxide precursor. Such a mixture typically comprises a ketone corresponding to the secondary alcohol used in each case, i.e. a ketone having the same carbon skeleton as the secondary alcohol used, e.g. acetophenone, acetone or cyclohexanone, a small amount of water and varying amounts of other active oxygen compounds, for example organic hydroperoxides.

The hydrogen peroxide used can also be generated in situ immediately before or during the epoxidation, as described, for example, in EP-B-0 526 945, JP-A-4 352 771, EP-B-0 469 662 and Ferrini et al. in "Catalytic Oxidation of Alkanes using Titanium Silicate in the Presence of in-situ Generated Hydrogen Ferroxide", DGMK Conference on Selective Oxidations in Petrochemistry, Sep. 16–18, 1992, p. 205–213.

Step (II)

This step of the process of the invention relates to the reaction of a compound having at least one C—C double bond or a mixture of two or more thereof with the hydroperoxide prepared in step (I) in the presence of a zeolite catalyst.

For the purposes of the present invention, "organic compound having a C—C double bond" encompasses all organic compounds having at least one C—C double bond. The compound in question may be a low molecular weight organic compound, i.e. a compound having a molecular weight of up to about 500, or a polymer, i.e. a compound having a molecular weight of more than 500. However, the process of the invention is preferably used for low molecular weight organic compounds of the type described above. These may be linear, branched or cyclic compounds which may contain aromatic, aliphatic, cycloaliphatic groups or a combination of two or more thereof. Preference is given to using an organic compound having from 2 to 30 carbon atoms, more preferably from 2 to 10 carbon atoms. The organic compound used is more preferably an aliphatic monoolefin. However, it is also possible for the organic compound used to have more than one ethylenically unsaturated double bond, as is the case, for example, in dienes or trienes. The compound may contain additional functional groups, such as halogen, carboxyl, an ester group, hydroxyl, an ether linkage, a sulfide linkage, carbonyl, cyano, nitro, amino or a combination of two or more thereof. The double bond may be terminal or internal. It may also be part of a cyclic structure, as is the case with cyclohexene. It is also possible to use a mixture of two or more of these compounds.

Further examples of suitable organic compounds include unsaturated fatty acids or derivatives thereof, such as esters and glycerides of such unsaturated fatty acids, and oligomers or polymers of unsaturated organic compounds, such as polybutadiene.

Examples of such organic compounds include: ethylene, propylene, 1-butene, cis- and trans-2-butene, isobutylene, butadiene, pentenes, isoprene, 1-hexene, 3-hexene, 1-heptene, 1-octene, diisobutylene, 1-nonene, 1-decene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, di-, tri- and tetramers of propylene, styrene and other vinylaromatic organic compounds having at least one C—C double bond, diphenylethylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinylcyclohexane, vinylcyclohexene, methallyl ketone, allyl chloride, allyl bromide, acrylic acid, methacrylic acid, crotonic acid, vinylacetic acid, crotyl chloride, methallyl chloride, dichlorobutenes, allyl alcohol, allyl carbonate, allyl acetate, alkyl acrylates and methacrylates, diallyl maleate, diallyl phthalate, unsaturated triglycerides, for example soybean oil, unsaturated fatty acids e.g. oleic acid, linoleic acid, linolenic acid, ricinoleic acid and esters thereof including mono-, di- and triglyceride esters.

Mixtures of two or more such compounds, especially mixtures of the compounds exemplified above, can also be used.

Thus, the present invention particularly provides a process of the present type where the organic compound having at least one C—C double bond is selected from the group consisting of a linear or branched aliphatic olefin, a linear or branched aromatic olefin, a linear or branched cycloaliphatic olefin, each having up to 30 carbon atoms, and a mixture of two or more thereof.

The process of the invention is particularly useful for reacting low molecular weight olefins, e.g. ethylene, propylene and the butenes, especially propylene.

Catalysts used in step (II) of the process of the invention are transition metal-containing, microporous and/or mesoporous and/or macroporous solids.

The oxidation of low molecular weight compounds in particular is preferably carried out using transition metal-containing microporous solids, particularly preferably zeolites containing transition metals, more preferably a zeolite containing titanium, zirconium, chromium, niobium, iron or vanadium, and especially a titanium silicalite.

Zeolites are crystalline aluminosilicates having ordered channel and cage structures with micropores. For the purposes of the present invention, "micropores" corresponds to the definition given in "Pure Appl. Chem." 45, p. 71ff., particularly p. 79 (1976), and refers to pores with a pore diameter of less than 2 nm. The network of such zeolites is composed of $SiO_4$ and $AlO_4$ tetrahedra which are linked by common oxygen linkages. A review of the known structures may be found, for example, in W. M. Meier and D. H. Olson in "Atlas of Zeolite Structure Types", Elsevier, 4th ed., London 1996.

Furthermore, there are zeolites which contain no aluminum and have Ti(IV) partly replacing Si(IV) in the silicate lattice. Titanium zeolites, especially those having a crystal structure of the MFI type, and possible ways of preparing them are described, for example, in EP-A-0 311 983 or EP-A-0 405 978. Apart from silicon and titanium, such materials may also contain further elements such as aluminum, zirconium, tin, iron, cobalt, nickel, gallium, boron or small amounts of fluorine.

The titanium in the zeolites described can be partly or wholly replaced by vanadium, zirconium, chromium, niobium or iron. The molar ratio of titanium and/or vanadium, zirconium, chromium, niobium or iron to the sum of silicon plus titanium and/or vanadium, zirconium, chromium, niobium or iron is usually in the range from 0.01:1 to 0.1:1.

Titanium zeolites having an MFI structure are known to be identifiable from a particular pattern in their X-ray diffraction diagrams and, in addition, from a skeletal vibration band in the infrared (IR) at about 960 $cm^{-1}$, and thus differ from alkali metal titanates or crystalline and amorphous $TiO_2$ phases.

Said titanium, zirconium, chromium, niobium, iron and vanadium zeolites are usually prepared by reacting an aqueous mixture of an $SiO_2$ source, of a titanium, zirconium, chromium, niobium, iron or vanadium source, e.g. titanium dioxide or an appropriate vanadium oxide, zirconium alcoxide, chromium oxide, niobium oxide or iron oxide, and of a nitrogenous organic base template, e.g. tetrapropylammonium hydroxide, with or without added basic compounds, in a pressure vessel at elevated temperature for several hours or some days, resulting in a crystalline product. The crystalline product is filtered off, washed, dried and baked at high temperature to remove the organic nitrogen base. In the resulting powder, the titanium or zirconium, chromium, niobium, iron and/or vanadium is present at least partly inside the zeolite framework in varying proportions in four-, five- or six-fold coordination. To improve the catalytic characteristics it is also possible to carry out a subsequent treatment by washing repeatedly with a solution of hydrogen peroxide containing sulfuric acid, after which the titanium or zirconium, chromium, niobum, iron, vanadium zeolite powder must be again dried and baked; this can be followed by a treatment with alkali metal compounds in order to convert the zeolite from the H form into the cation form. The resulting titanium or zirconium, chromium, niobium, iron, vanadium zeolite powder is then processed into a shaped body as described below.

Preferred zeolites are titanium, zirconium, chromium, niobium or vanadium zeolites, more preferred zeolites are those having a pentasil structure, especially the types with X-ray assignment to a BEA, MOR, TON, MTW, FER, MFI, MEL, CHA, ERI, RHO, GIS, BOG, NON, EMT, HEU, KFI, FAU, DDR, MTT, RUT, LTL, MAZ, GME, NES, OFF, SGT, EUO, MFS, MCM-22 or MFI/MEL mixed structure. Zeolites of this type are described, for example, in the above Meier and Olson reference. Also possible for the present invention are titanium-containing zeolites having the structure of UTD-1, CIT-1, CIT-5, ZSM-48, MCM-48, ZSM-12, ferrierite or β-zeolite and of mordenite. Such zeolites are described, inter alia, in U.S. Pat. No. 5,430,000 and WO 94/29408, the relevant contents of which are incorporated herein by reference in their entirety.

Nor are there special restrictions in the pore structure of the catalysts used according to the invention, i.e. the catalyst can have micropores, mesopores, macropores, micro- and mesopores, micro- and macropores or micro-, meso- and macropores, the definition of "mesopores" and "macropores" also corresponding to the definition given in the Pure Appl. Chem. reference given above and referring to pores having a diameter of from >2 nm to about 50 nm or >about 50 nm, respectively.

The catalyst used according to the invention can also be a material based on a mesoporous oxide containing at least one transition metal and silicon or of a xerogel containing a transition metal and silicon.

Particular preference is given to silicon-containing mesoporous oxides which additionally contain Ti, V, Zr, Sn, Cr, Nb or Fe, especially Ti, V, Zr, Cr, Nb or a mixture of two or more thereof.

If low molecular weight olefins such as, for example, propylene are reacted in the present invention, particular preference is given to using titanium-containing zeolite catalysts having exclusively or virtually exclusively micropores such as, for example, titanium silicalite 1, titanium silicalite 2 or titanium-containing zeolite β, more preferably titanium silicalite 1 or titanium silicalite 2, especially titanium silicalite 1.

The use of a catalyst having particular mechanical stability is preferred, if the reaction of step (II) is carried out as a fixed-bed process. Particularly suitable for this purpose are catalysts having zeolite structure as described in DE-A-196 23 611, which is incorporated herein by reference in its entirety with respect to the catalysts described therein.

These catalysts are based on titanium or vanadium silicates having zeolite structure. As regards the zeolite structure, reference is made to the above-mentioned preferred structures. These catalysts are characterized in that they have been shaped by strengthening shaping processes.

Suitable strengthening shaping processes which can be used include in principle all strengthening shaping methods customarily used for catalysts. Preference is given to processes wherein shaping is done by extruding in customary extruders, for example to obtain extrudates having a diameter of usually from 1 to 10 mm, especially from 2 to 5 mm. If binders and/or adjuvants are needed, extruding is advantageously preceded by a mixing or kneading procedure. Extrusion may be followed by a calcining step. The resulting extrudates are comminuted, if desired, preferably to obtain pellets or granules having a particle diameter of from 0.5 to 5 mm, especially from 0.5 to 2 mm. Pellets, granules and also shaped catalyst bodies formed in a different manner contain virtually no finer fractions than those having a minimum particle diameter of 0.5 mm.

In a preferred embodiment the shaped oxidation catalyst used contains up to 10% by weight of binder, based on the total mass of the catalyst. Particularly preferred binder contents are from 0.1 to 7% by weight, especially from 1 to 15% by weight. Suitable binders are in principle all compounds used for this purpose; preference is given to compounds, especially oxides, of silicon, aluminum, boron, phosphorus, zirconium and/or titanium. A binder of particular interest is silicon dioxide, which may be introduced into the shaping step in the form of silica sol or tetraalkoxysilanes. Oxides of magnesium and beryllium and also clays, e.g. montmorillonites, kaolins, bentonites, halloysites, dickites, nacrites and anauxites, can also be used as binders.

Adjuvants for the strengthening shaping processes include, for example, extrusion adjuvants, a customary extrusion adjuvant being methylcellulose. Such adjuvants are usually burnt off completely in a subsequent calcining step.

The above-mentioned titanium and vanadium zeolites are typically prepared as described above in the general description of the zeolite catalysts used according to the invention. The resulting titanium or vanadium zeolite powder is then shaped as described above.

It is also possible to regenerate oxidation catalysts based on titanium or vanadium silicates having zeolite structure and containing from 0.01 to 30% by weight of one or more noble metals from the group consisting of ruthenium, rhodium, palladium, osmium, iridium, platinum, rhenium, gold and silver, which are also characterized in that they have been shaped by strengthening shaping processes. Such catalysts are disclosed in DE-A-196 23 609, which is incorporated herein by reference in its entirety for the catalysts described therein.

What was said above in connection with DE-A-196 23 611 applies with regard to the strengthening shaping processes, the binders and the adjuvants and the structure of the oxidation catalysts.

The catalyst disclosed in DE-A-196 23 609 contains from 0.01 to 30% by weight, especially from 0.05 to 15% by weight, and in particular from 0.01 to 8% by weight, of the above-mentioned noble metals, in each case based on the amount of the titanium or vanadium zeolites. Particular preference is given to palladium. The noble metals can be applied to the catalyst in the form of suitable noble metal components, for example in the form of water-soluble salts before, during or after the strengthening shaping step.

In many cases it is most advantageous, however, to apply the noble metal components to the shaped catalyst bodies only after the shaping step, especially if a high temperature treatment of the noble metal catalyst is undesirable. The noble metal components can be applied to the shaped catalyst particularly by ionexchange, impregnation or spraying. The application may be carried out using organic solvents, aqueous ammonia solutions or supercritical phases such as, for example, carbon dioxide.

It is quite possible to produce noble metal catalysts of various types by means of the methods mentioned above. Thus, a type of coated catalyst can be produced by spraying the shaped catalyst bodies with the noble metal solution. The thickness of this noble metal surface layer can be increased considerably by impregnating, whereas the catalyst particles are coated substantially uniformly with noble metal across the cross section of the shaped bodies in the case of ion-exchange.

In the process of the invention, greater preference is given to using a zeolite catalyst obtainable by a process which comprises the following steps:

(i) admixing a mix comprising a zeolite or a mix of two or more thereof with a mixture comprising at least one alcohol and water, and (ii) kneading, shaping, drying and calcining of the admixture of step (i).

In step (i) of this catalyst preparation process, a zeolitic material, preferably the zeolites described in more detail hereinbefore, in particular the titanium or vanadium zeolites described in more detail hereinabove, is processed with a mixture comprising at least one alcohol and water, a binder, optionally one or more organic viscosity enhancers and other prior art additives to obtain a plastically deformable material. This plastically deformable material obtained by intimate mixing, especially kneading, of the above-mentioned components is then shaped, preferably by extrusion, and the resulting shaped body is dried and finally calcined.

The catalyst which is particularly preferably used according the invention and its preparation may be more particularly described as follows:

The zeolite used according to the invention is preferably a titanium-, zirconium-, chromium-, niobium-, iron- or vanadium-containing zeolite and especially a titanium silicalite, which in turn is preferably a microporous titanium silicalite, more preferably a microporous titanium silicalite having pentasil zeolite structure. What was said in the general description of the zeolite used according to the invention regarding the composition, structure, pore distribution and preparation of the zeolites also applies here.

Suitable binders include in principle all compounds hitherto used for this purpose. Preference is given to compounds, especially oxides of silicon, aluminum, boron, phosphorus, zirconium and/or titanium. A binder of particular interest is silicon dioxide which may be introduced into the shaping step in the form of silica sol or tetraalkoxysilanes. Oxides of magnesium and beryllium and also clays, e.g. montmorillonites, kaolins, bentonites, halloysites, dickites, nacrites and ananxites, can also be used as binders.

Preferred binders added in step (I) of the process of the invention are, however, a metal acid ester or a mixture of two or more thereof. Particular examples of these are orthosilicates, tetraalkoxysilanes, tetraalkoxytitanates, trialkoxyaluminates, tetraalkoxyzirconates or a mixture of two or more thereof.

Particularly preferred binders are tetraalkoxysilanes. Specific examples are tetramethoxysilane, tetraethoxysilane, tetrapropoxysilane and tetrabutoxysilane, the corresponding tetraalkoxytitanium and tetraalkoxyzirconium compounds and trimethoxy-, triethoxy-, tripropoxy-, tributoxyaluminum, with tetramethoxysilane and tetraethoxysilane being especially preferred.

The catalyst which is particularly preferably used according to the invention in the form of a shaped body contains preferably up to about 80% by weight, more preferably from about 1 to about 50% by weight, especially from about 3 to about 30% by weight, of binder, in each case based on the total mass of the shaped body, the binder content being calculated on the basis of the amount of metal oxide formed.

The metal acid ester which is preferably used is used in such an amount that the resulting metal oxide content in the solid is from about 1 to about 80% by weight, preferably from about 2 to about 50% by weight, especially from about 3 to about 30% by weight, in each case based on the total mass of the shaped body.

As can already be seen from the above, mixtures of two or more of the above-mentioned binders can also be used.

It is essential to use a mixture containing at least one alcohol and water as pasting aid when preparing this shaped body. The alcohol content of this mixture is generally from about 1 to about 80% by weight, preferably from about 5 to about 70% by weight, in particular from about 10 to about 60% by weight, in each case based on the total weight of the mixture.

The alcohol used is preferably the same as the alcohol component of the metal acid ester preferably used as a binder, but the use of another alcohol is not critical either.

Any alcohol can be used, provided it is water-miscible. Accordingly, monoalcohols having from 1 to 4 carbon atoms and water-miscible polyhydric alcohols can be used. Use is made in particular of methanol, ethanol, propanol and n-, iso- and tert-butanol and mixtures of two or more thereof.

Usable organic viscosity enhancers likewise include all prior art substances suitable for this purpose. Preference is given to organic, especially hydrophilic, polymers such as cellulose, starch, polyacrylates, polymethacrylates, polyvinyl alcohol, polyvinylpyrrolidone, polyisobutene and polytetrahydrofuran. These substances promote primarily the formation of a plastically deformable material during the kneading, shaping and drying step by bridging the primary particle and additionally ensure the mechanical stability of the shaped body during shaping and drying. These substances are removed from the shaped body during calcining.

Further additives that can be added are amines or amine-like compounds such as tetraalkylammonium compounds or aminoalcohols and carbonate-containing substances such as calcium carbonate. Such further additives are disclosed in EP-A-0 389 041, EP-A-0 200 260 and in WO 95/19222, the relevant contents of which are incorporated herein by reference in their entirety.

It is also possible to use acidic additives instead of basic additives. Among other things, these acidic compounds can cause a faster reaction of the metal acid ester with the porous oxidic material. Preference is given to organic acidic compounds which can be baked out by calcining after the shaping step. Carboxylic acids are particularly preferred. It is also possible to include mixtures of two or more of the above-mentioned additives.

The sequence in which the components of the material containing the porous oxidic material are added is not critical. It is possible to add the binder first, followed by the organic viscosity enhancer and the additive, if used, and finally the mixture containing at least one alcohol and water, but also to change the sequence of binder, organic viscosity enhancer and additives.

Following the addition of the binder to the pulverulent porous oxide to which the organic viscosity enhancer may have been added, the usually still pulverulent material is homogenized in a kneader or extruder for 10 to 180 minutes. This is generally done at from about 10° C. to the boiling point of the pasting aid and at atmospheric pressure or slight superatmospheric pressure. Subsequently, the remaining components are added, and the resulting mixture is kneaded until a plastically extrudable material has formed.

Kneading and shaping can in principle be carried out using any of the numerous customary prior art kneading and shaping apparatuses or processes generally used for the preparation of, for example, shaped catalyst bodies.

As indicated above, preference is given to processes wherein the shaping is carried out as extrusion from customary extruders, for example to form extrudates having a diameter of typically from about 1 to about 10 mm, especially from about 2 to about 5 mm. Such extruders are described, for example, in "Ullmanns Enzyklopädie der Technischen Chemie", 4th edition, vol. 2, p. 295ff, 1972.

Following extrusion, the resulting shaped bodies are dried at from generally about 30° C. to about 140° C. (from 1 to 20 h, atmospheric pressure) and calcined at from about 400° C. to about 800° C. (from 3 to 10 h, atmospheric pressure).

It is possible to comminute the resulting extrudates. They are preferably comminuted to obtain pellets or granules having a particle diameter of from 0.1 to 5 mm, especially from 0.5 to 2 mm.

These pellets or granules and also shaped particles formed in a different manner contain virtually no finer fractions than those having a minimum particle diameter of about 0.1 mm.

Although there are no special limitations concerning the apparatus used for the reaction, step (II) of the process of the invention is preferably carried out in a reactor battery which is packed with one of the catalysts which can be used according to the invention, consisting of from two to seven, preferably from two to five, reactors, the catalyst being in the form of a tablet or an extrudate forming a fixed bed or in the form of a powder forming a suspension. Examples of usable reactor types that may be mentioned are stirred tank reactors and tubular reactors with or without external circulation.

In the reaction, a hydroperoxide-containing, preferably hydrogen peroxide-containing stream comprising an organic compound having at least one C—C double bond, preferably a $C_2$–$C_4$-olefin, more preferably propylene, is contacted with an organic solvent, preferably a $C_1$–$C_6$-alcohol, especially preferably methanol, and converted to the desired oxidized compound, preferably to the epoxide, at from about 20° C. to about 120° C., preferably from about 30 to about 80° C. The preferred solvent methanol used can be fresh methanol or methanol recycled from the epoxidation.

The ratio of the compound to be reacted to the hydroperoxide is not critical and is in a molar ratio of from about 100:1 to about 1:10, preferably from about 1:1 to about 6:1.

The hydroperoxide content in the reactor (without compound to be reacted) is generally from about 0.1 to about 10%, the methanol content is from about 10 to 90%, and the water content is from about 5 to about 50%.

The amount of catalyst present in the reactor may also be varied within wide limits. The amount of catalyst present should be sufficient to complete the desired reaction within a short period of time. The optimum amount depends on many factors such as temperature, ratio between compound to be reacted and hydroperoxide, reactivity of the compound to be reacted, reaction pressure, residence time, and flow rates of the compounds introduced into the reactor. The reaction temperature is generally within the range from about 20° C. to about 120° C., preferably from about 30° C. to about 100° C., more preferably from about 30° C. to about 80° C. The temperature should generally be chosen so that the desired reaction can be carried out within an economically viable period of time. The residence time is generally within the range from about 10 min to about 24 h, preferably from about 10 min to about 1 h, per reactor. The reaction pressure is generally chosen in the range from about 1 to about 100 bar, preferably from about 15 to about 40 bar. The reaction mixture is preferably in liquid form. The reaction temperature, residence time and reaction pressure should be selected so that the hydroperoxide conversion is at least 50%, preferably at least 90%, in particular 99% or more.

After the reaction has ended, the oxidation product formed may be separated from water, solvent and any byproducts. The separation may be carried out by all prior art separation methods, preference being given to distillative separation methods.

Any unconverted organic compound having at least one C—C double bond and the solvent obtained can likewise be separated off and recycled to the reaction of step (II) if desired.

The reaction of step (II) may be carried out continuously, batchwise or part-continuously depending on the reactor used, for example a fixed bed, a moving bed, a liquid bed or else as a suspension procedure in a stirred or unstirred manner. It is also possible to carry out the reaction in a one-phase or a multiphase system, as e.g. a two-phase system. This reaction is preferably carried out as a fixed-bed process.

Once the epoxidation has progressed to a certain degree, the desired oxidation product may be separated from the reaction mixture by any prior art separation method capable of separating the oxidation product from the reaction mixture. Preference is given to using distillative separation methods.

The resulting oxidation product is obtained essentially free from the catalyst used, especially when conducting the reaction as a fixed-bed process, and may thus be worked up further without additional catalyst separation steps.

Unconverted starting material, i.e. the organic compound having at least one C—C double bond or the mixture of two or more thereof and unconverted hydroperoxide, can be separated off and recycled in the same manner or cracked to form products such as water or alcohol and oxygen, for example.

In certain embodiments of the present invention, especially when preparing the hydroperoxide starting from a secondary alcohol, in which case the hydroperoxide-containing mixture used for oxidation also contains a secondary alcohol or the corresponding ketone, the latter can in turn be converted to the secondary alcohol by a hydrogenation step and recycled into the epoxidation of step (I). Hydrogenation reactions of this type are well known in the art, and the hydrogenation is preferably conducted over a transition metal catalyst containing, for example, Raney nickel, ruthenium or palladium.

It is also possible to dehydrogenate the secondary alcohol, if present, by known methods to obtain additional products of value such as styrene, for example.

Step (III)

This step relates to the regeneration of the at least partially deactivated zeolite catalyst used in step (II).

The activity of the catalyst decreases with increasing reaction time owing to increasing deposits which are mostly of organic origin. These deposits which are in particular organic, can be, inter alia, oligomers or polymers of the oxidation product formed, e.g. propylene oxide. In the process of the present invention, the catalyst is regenerated if its activity falls below a certain threshold value. This threshold value generally corresponds to an activity of 60% or less, preferably 40% or less, and especially 20% or less, in each case based on the initial activity of the catalyst to be regenerated.

If the process of the invention is carried out in suspension, i.e. using a zeolite catalyst in the form of a powder, the catalyst may be separated from the reaction mixture by customary solid/liquid separation methods such as simple filtration, cross-flow filtration, centrifugation, etc. and regenerated. The regeneration is preferably carried out by continuously separating and regenerating the catalyst present in the reactor and recycling it into the reactor in regenerated form.

If the zeolite catalyst in the reactor is packed as a fixed bed, the regeneration is advantageously conducted in the reactor itself, i.e. the catalyst is not removed but remains in the fixed bed in the reactor in a packed state.

To recover product of value present on the catalyst, the catalyst may further be washed with a solvent for the product of value obtained after the reaction of step (II) and before the regeneration of step (III). Solvents which can be used for washing include all solvents capable of dissolving the product of value which is desired in each case. Particular examples of solvents are water, alcohols, aldehydes, ketones, ethers, acids, esters, nitrites, hydrocarbons and mixtures of two or more thereof as discussed hereinafter in the discussion of the preferred variation of regeneration in the present invention.

Generally, the catalyst is then heated in a stream of inert gas either in the reactor or separately to effect regeneration. Oxygen is added to the stream of inert gas once a certain temperature is reached. This temperature is generally from about 200 to about 800° C., preferably from about 250 to 600° C., and more preferably from about more than 400 to about 600° C. The amount of oxygen added to the inert gas is regulated in such a manner that the temperature during regeneration, which temperature increases owing to the heat generated by burning off the mostly organic deposits, does not exceed about 800° C., preferably about 600° C., more preferably about 550° C., and does not fall below about 400° C., preferably about 450° C., so that the regeneration proceeds sufficiently rapidly on the one hand and irreversible damage to the catalyst framework is avoided on the other hand.

Following the complete removal of the deactivating, mostly organic deposits which is indicated by decreasing catalyst temperature in spite of increasing oxygen content at the outlet of the regenerator, the catalyst is cooled down slowly, again under inert gas.

As indicated above, the regeneration of step (III) is carried out in an inert gas atmosphere containing oxygen or oxygen-supplying substances. The term oxygen-supplying substance encompasses all substances which are capable of releasing oxygen or removing carbonaceous residues under the indicated regeneration conditions. The atmosphere is preferably a nitrogen-containing atmosphere comprising oxygen or an oxygen-supplying substance. The oxygen-supplying substance is preferably a nitrogen oxide of the formula $N_xO_y$, where x and y are selected so that the nitrogen oxide is neutral, $N_2O$, an $N_2O$-containing waste gas stream produced by an adipic acid plant, NO, $NO_2$, ozone or a mixture of two or more thereof.

If $CO_2$ is used, the temperature is in the range from 500 to 800° C.

The oxygen content in the gas mixture used for regeneration is preferably less than about 50% by volume, more preferably less than about 30% by volume, especially less than about 10% by volume, most preferably less than about 5% by volume.

In a further embodiment of the process of the invention, the gas stream may be moistened with steam or solvent vapor when the regenerated catalyst has cooled down to below about 200° C., preferably about 150° C., more preferably about 100° C. The solvents which may be used for this purpose include the same solvents as may be used for washing the at least partially deactivated catalyst before the actual regeneration. Preferred solvents are described hereinafter in more detail in the discussion of the preferred regeneration of step (III) of the process of the invention.

After reaching the reaction temperature at which step (II) is carried out and after sufficient solvent moistening, if performed, the regenerated catalyst is introduced into the reactor and the reactor is charged with the solvent for the oxidation and reused for the reaction of step (II). If the catalyst remains in the reactor as a fixed bed during regeneration, the reactor is filled with the solvent for the oxidation and the reaction of step (II) is carried out.

A preferred embodiment of the regeneration of an at least partially deactivated zeolite catalyst according to step (III) is described in detail hereinafter.

In this embodiment, the regeneration comprises the following steps:
(a) heating an at least partially deactivated catalyst to 250° C.–600° C. in an atmosphere containing less than 2% by volume of oxygen, and
(b) subjecting the catalyst to a gas stream containing an oxygen-generating substance or oxygen or a mixture of two or more thereof in an amount in the range from 0.1 to 4% by volume at from 250 to 800° C., preferably from 350 to 600° C.

This preferred regeneration preferably comprises a further step (c):
(c) subjecting the catalyst to a gas stream containing an oxygen-generating substance or oxygen or a mixture of two or more thereof in an amount in the range from 4 to 100% by volume at from 250 to 800° C., preferably from 350 to 600° C.

The regeneration is conducted in essentially the same manner when regenerating catalysts in the form of powders which have been used as suspension, when regenerating catalysts packed in a fixed bed in the form of a shaped particle, and when regenerating catalysts crystallized on nets, for example stainless steel, Kanthal or packings, and surface-coated catalysts consisting of an inert core comprising $SiO_2$, $\alpha$-$Al_2O_3$, highly calcined $TiO_2$, steatite and an active catalyst surface layer comprising a zeolite, preferably a zeolite as defined above.

If the catalyst has been used in suspension, it must first be separated from the reaction solution by a separation step, for example filtration or centrifugation. The resulting, at least partially deactivated pulverulent catalyst can then be regenerated. Using such pulverulent catalysts, the steps carried out at elevated temperatures during the regeneration process are preferably conducted in rotary tube ovens. When regenerating a catalyst used in suspension, it is especially preferred to combine the suspension reaction and the regeneration process of the invention by continuously removing some of the at least partially deactivated catalyst from the reaction, externally regenerating it using the process of the invention and recycling the regenerated catalyst into the suspension reaction.

As well as regenerating catalysts in the form of powders, it is also possible to regenerate catalysts in the form of shaped bodies, for example shaped bodies packed in a fixed bed. The regeneration of a catalyst packed in a fixed bed is preferably carried out in the reactor itself without the need to discharge or introduce the catalyst so that it is not subjected to any additional mechanical stress. The regeneration of the catalyst in the reactor itself involves stopping the reaction, removing any reaction mixture present, regenerating and then continuing the reaction.

According to step (a) the catalyst is heated to from about 250° C. to about 600° C., preferably about 400° C.–550° C., especially about 450° C.–500° C., in an atmosphere containing less than 2% by volume, preferably less than 0.5% by volume, especially less than 0.2% by volume, of oxygen, either in the reactor or in an external oven. The heating of step (a) is preferably carried out at a heating rate of from about 0.1° C./min to about 20° C./min, preferably from about 0.3° C./min to about 15° C./min, especially 0.5° C./min–10° C./min.

In this heating phase, the catalyst is heated to a temperature at which the mostly organic deposits present begin to decompose while at the same time the temperature is controlled via the oxygen content and does not increase so as to damage the catalyst structure.

Once the temperature range from about 250° C. to about 800° C., preferably from about 350° C. to about 600° C., especially from about 400° C. to about 600° C., which is desired for the decomposition of the deposits, is reached, the catalyst may be left at these temperatures in the atmosphere defined above if desired or if necessary owing to the presence of a large amount of organic deposits.

In step (a) of the regeneration, if desired in combination with leaving the catalyst at the indicated temperature, the bulk of the deposits is coked. This step involves the removal from the catalyst of the substances formed in this process, for example hydrogen, water, carbonaceous substances. The removal of the deposits by coking in this step reduces significantly the amount of energy generated during the burnoff of the catalyst in steps (b) and possibly (c) of the process of the invention by subjecting the catalyst to a gas stream containing more oxygen, so that the slow heating of step (a) of the process of the invention is in itself an essential step in the prevention of local overheating of the catalyst.

In step (b) of this regeneration, the catalyst is then subjected to a gas stream containing an oxygen-generating substance or oxygen or a mixture of two or more thereof in an amount in the range from about 0.1 to about 4% by volume, preferably from about 0.1 to about 3% by volume, more preferably from about 0.1 to about 2% by volume, at from about 250° C. to about 800° C., preferably from about 350° C. to about 600° C.

The amount of molecular oxygen or oxygen-supplying substances added is critical in that the amount of energy generated in this step through burnoff of the coked organic deposits is accompanied by an increase in catalyst temperature, so that the temperature in the regenerator must not depart from the desired temperature range from about 250° C. to about 800° C., preferably from about 350° C. to about 600° C. The amount of molecular oxygen or oxygen-supplying substances is chosen in such a manner that the temperature in the apparatus is in the range from about 400° C. to about 500° C.

With increasing burnoff of the deposits the content of molecular oxygen or oxygen-supplying substances in the stream of inert gas must be increased up to 100% by volume to maintain the temperature required for regeneration so that after completion of step (b) the catalyst is subjected, in step (c), to a gas stream containing an oxygen-supplying substance or oxygen or a mixture of two or more thereof in an amount in the range from more than about 4 to about 100% by volume, preferably from more than about 3 to about 20% by volume, more preferably from about 2 to about 20% by volume, in the temperature range defined for step (b).

A procedure is usually followed here in which the amount of oxygen or oxygen-supplying substance in the feed gas stream is continuously increased as the temperature in step (b) decreases.

The temperature of the catalyst itself is maintained at a temperature range from about 250° C. to about 800° C., preferably from about 350° C. to about 600° C., especially from about 400° C. to about 600° C., by appropriately controlling the oxygen content or the content of oxygen-supplying substances in the gas stream.

The burnoff of the organic deposits is complete when the temperature of the effluent gas stream at the reactor outlet decreases in spite of increasing amounts of molecular oxygen or oxygen-supplying substances in the gas stream. The duration of the treatment according to step (b) and step (c), if necessary or desired, is generally from about 1 to about 30 hours, preferably from about 2 to about 20 hours, especially from about 3 to about 10 hours, in each case.

The term "oxygen-supplying substances" is defined as above.

In another embodiment of the process of the invention the at least partially deactivated catalyst is washed with a solvent to remove product of value still adhering to the catalyst prior to the heating of step (a). Washing is carried out in such a way that the products of value adhering to the catalyst are each removable there-from, but the temperature and pressure are not sufficiently high to remove the mostly organic deposits as well. The catalyst is preferably merely rinsed with a suitable solvent.

Suitable solvents for this washing procedure include thus all solvents in which the actual reaction product is readily soluble. Such solvents are preferably selected from the group consisting of water, an alcohol, e.g. methanol, ethanol, 1-propanol, 2-propanol, 2-methyl-2-propanol, 1-butanol, 2-butanol, allyl alcohol or ethylene glycol, an aldehyde, e.g. acetaldehyde or propionaldehyde, a ketone, e.g. acetone, 2-butanone, 2-methyl-3-butanone, 2-pentanone, 3-pentanone, 2-methyl-4-pentanone or cyclohexanone, an ether such as diethyl ether or THF, an acid, e.g. formic acid, acetic acid or propionic acid, an ester, e.g. methyl formate, methyl acetate, ethyl acetate, butyl acetate or ethyl propionate, a nitrile, e.g. acetonitrile, a hydrocarbon, e.g. propane, 1-butene, 2-butene, benzene, toluene, xylene, trimethylbenzene, dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, dibromoethane, allyl chloride or chlorobenzene, and mixtures of two or more thereof, if miscible.

Preference is given to solvents which already act as solvents in the reaction, e.g. olefin epoxidation using the catalyst to be regenerated. Examples of such solvents for the epoxidation of olefins are: water, alcohols, e.g. methanol, ethanol, 1-propanol, 2-propanol, 2-methyl-2-propanol, 1-butanol, 2-butanol, allyl alcohol or ethylene glycol or ketones, e.g. acetone, 2-butanone, 2-methyl-3-butanone, 2-pentanone, 3-pentanone, 2-methyl-4-pentanone or cyclohexanone.

The amount of solvent used and the duration of the washing procedure are not critical, but the amount of solvent and the duration of the washing procedure should be sufficient to remove the bulk of the product of value adhering to the catalyst. The washing procedure can be carried out at the temperature of the reaction or at higher temperatures, but the temperature should not be so high that the solvent used for washing itself reacts with the product of value to be removed. If temperatures higher than the reaction temperature are used, a range from 5° C. to 150° C. above the reaction temperature, in particular also depending on the boiling point of the solvents used, is generally sufficient. The washing procedure can be repeated more than once, if necessary. The washing procedure can be carried out under atmospheric pressure, under elevated pressure or even under supercritical pressure. Preference is given to atmospheric pressure or elevated pressure. If $CO_2$ is used as solvent, preference is given to supercritical pressure.

If a pulverulent catalyst which has been used in suspension is regenerated, the removed catalyst is washed in an external reactor. If the catalyst is packed in a reactor as a fixed bed, washing may be carried out in the reactor used for the reaction. In this case, the reactor containing the catalyst to be regenerated is rinsed one or more times with a solvent to recover residual product of value. Subsequently, the solvent is removed from the reactor.

The catalyst is generally dried on completion of the washing procedure. The drying procedure is not critical per se, but the drying temperature should not too greatly exceed the boiling temperature of the solvent used for washing to avoid abrupt evaporation of the solvent in the pores, especially any micropores of the zeolite catalyst, since this can also damage the catalyst. In the regeneration of pulverulent catalysts, drying is again carried out externally in a heating apparatus under inert gas atmosphere. In the case of catalysts in a fixed bed, the catalyst in the reactor is subjected to an inert gas stream at moderate temperatures. It is possible, but not necessary, to dry the catalyst completely. Pulverulent catalysts are usually dried until the powder is flowable. Nor is it necessary to dry fixed-bed catalysts completely.

In another embodiment of this regeneration, the regenerated catalyst obtained in step (c) is cooled down in an inert gas stream in an additional step (d). This inert gas stream may contain up to about 20% by volume, preferably from about 0.5 to about 20% by volume, of a vapor of a liquid selected from the group consisting of water, an alcohol, an aldehyde, a ketone, an ether, an acid, an ester, a nitrile, a hydrocarbon as decribed above in the context of washing the catalyst, and a mixture of two or more thereof. Preference is given to using water, alcohol or a mixture of two or more thereof as vapor of a liquid.

As regards the preferably usable alcohols, aldehydes, ketones, ethers, acids, esters, nitrites or hydrocarbons, reference is made to the corresponding discussion of the solvents which can be used in the washing procedure of the process of the invention.

It is also important to cool down slowly when carrying out the cooling operation of step (d), since cooling down too fast (quenching) can adversely affect the mechanical strength of the catalyst. The mechanical properties of the catalyst can also be adversely affected by rapid rinsing of the regenerated, dry shaped catalyst bodies during restart of the reactor for further reaction. For this reason, it is advisable to add the vapor of a liquid as defined above during the cooling phase. It is more preferable, however, not to add the vapor until the temperature is below a threshold temperature which is defined by the boiling point of the liquid used for the vapor. The threshold temperature is usually below about 250° C., preferably below about 200° C., especially below about 150° C.

After the regeneration the catalyst may be treated by basic and/or silylating compounds in order to remove acidic centers. Particularly suitable compounds are diluted aqueous solutions of alkaline or alkaline earth hydroxides, alkaline or alkaline earth carbonates, alkaline or alkaline earth hydroxy carbonates; Li, K, Na acetates and phosphates; and silylating esters, such as tetraalkoxy silane, tetraalkoxymonoalkyl silane and hexamethylene disilane.

Step (IV)

This step relates to reusing the catalyst regenerated according to step (III). To this end, the regenerated catalyst is recycled into the reactor (if the at least partially deactivated catalyst has been regenerated externally) and the reaction is carried out or continued as described in step (II).

If the regeneration has been carried out in the reactor, the reaction is continued as described in step (II) on completion of the regeneration.

If, in the process of the invention, the organic compound having at least one C—C double bond is selected from the group consisting of a linear or branched aliphatic olefin, a linear or branched aromatic olefin and a linear or branched cycloaliphatic olefin, each having up to 30 carbon atoms, i.e. if an olefin is reacted with the hydroperoxide, this olefin can be obtained by dehydrogenating the corresponding saturated organic compound to form the olefin and hydrogen.

Processes of this type for converting an alkane to the corresponding olefin are known per se, in particular with respect to propane dehydrogenation. These processes are known in the literature as STAR, CATOFIN® or OLEFLEX® processes and are described in detail, for example, in Chem. Systems Report 91–5, 1992, p. 50ff., and also referred to in numerous patents, e.g. U.S. Pat No. 4,665,267 or EP-A 0 328 507 and U.S. Pat, No. 4,886,928.

These processes are characterized by an endothermic reaction cleaving the alkane to form the olefin, i.e. propane to propene, for example, and hydrogen. Widely used catalysts are zinc and aluminum spinels doped with noble metals, chromium oxide/aluminum oxide, and also supported platinum catalysts.

Furthermore, promoted iron oxide catalysts for alkane dehydrogenations are known from DE-A 39 23 026.

The olefin wich is preferably used as starting material, in particular propylene, can also be obtained starting from the corresponding saturated hydrocarbon by steam cracking, catalytic cracking. Such processes are described in more detail, inter alia, in U.S. Pat. Nos. 5,599,955 and 5,599,956 mentioned at the beginning, and in the prior art cited therein, both these references including the prior art cited therein being incorporated herein by reference in their entirety.

In the process of the invention, especially when carried out as an integrated process, i.e. a process in which all volume streams are closed loops, it is advantageous to obtain the olefin, especially propylene, to be used in the epoxidation step by dehydrogenating the corresponding saturated organic compound, since the epoxidation step tolerates the unreacted alkane which is present in addition to the olefin and which comes from the dehydrogenation step and thus renders a costly alkane/olefin separation, especially a propane/propene separation, unnecessary.

The hydrogen from the alkane dehydrogenation can also be directly used in the hydrogen peroxide formation, for example according to the anthraquinone process described at the beginning or the process starting from the elements as described at the beginning in the discussion of step (I) of the process of the invention.

The endothermic alkane dehydrogenation step can also be coupled with the exothermic reaction of step (II) in an integrated heat and energy system.

As indicated above, the process of the invention is particularly suitable as an integrated process, i.e. a multistep process wherein the streams of the various components used in the process are partially or completely closed loops, more preferably in combination with an appropriate integrated heat and energy system in which the amounts of energy generated in the exothermic process steps (II) and (II) can be used directly for running the endothermic step (I).

The Examples which follow illustrate the invention.

EXAMPLES

Example 1

Synthesis of Hydrogen Peroxide by the Anthraquinone Process 10 kg of a Pd on carbon hydrogenation catalyst (10% by weight of palladium) were added to 600 kg of a working solution consisting of about 10% by weight of 2-ethyl-anthraquinone dissolved in a mixture of 70% by volume of Shellsol NF and 30% by volume of tetrabutylurea and the mixture was contacted with hydrogen at 1.5–2 bar at 45° C. in a stirred tank until the theoretical hydrogen consumption had been reached. The solution which was now black was cooled to room temperature and the catalyst separated off by filtration. The hydroquinone-containing solution was oxidized with diluted air (10% by volume of oxygen, 90% by volume of nitrogen) in three batches of 200 kg each in a jet tube reactor until the hydrogen peroxide content was constant. Following the oxidation, about 15 kg of DI water were added to 200 kg of the mixture which now contained about 1% by weight of hydrogen peroxide, and this mixture was stirred vigorously for 15 min. The aqueous phase was then separated off. This aqueous solution now containing about 9% by weight of hydrogen peroxide was stirred vigorously with the next 200 kg batch for 15 min. Separation gave a mixture having a hydrogen peroxide content of about 15% by weight which was used to extract the last 200 kg batch in the same manner. This procedure gave about 15 kg of an aqueous solution containing about 20% by weight of hydrogen peroxide.

Better hydrogen peroxide yields may be obtained using a continuous counterflow extraction, for example in a sieve-plate column, a pulsed sieve-plate column or a packed column.

Example 2

Synthesis of Hydrogen Peroxide According to DE-A 196 42 770

In the preparation of hydrogen peroxide according to the above-mentioned application, the reaction vessel used was a 270 ml autoclave equipped with stirrer, thermostating and pressure regulation to 50 bar. This reactor was fitted with a catalyst monolith, centered around the stirrer axis so that the stirrer supplied the monolith uniformly with liquid and gas, prepared as follows. Feed lines for oxygen, hydrogen and the reaction medium were located in the base of the reactor. A discharge line from which the product/gas mixture could be continuously discharged was located in the lid of the reactor. After subtraction of the volumes of all internals an effective reaction volume of 208 ml was available.

The catalyst monolith used was prepared as follows:

A corrugated net and a smooth net of V4A steel (1.4571, mesh size 180 μm, wire diameter 146 μm) were placed on top of each other and rolled up to give a cylindrical monolith 5 cm high and 5 cm in diameter. The ends of the nets were fixed by weld points. The distance between the the ends of the smooth nets was at least 1 mm.

The monolithic support was treated in succession with acetone and distilled water and then dried. The monolith was then treated with a solution of 25% by weight of concentrated hydrochloric acid and 75% by weight of distilled water at 60° C. for 10 min and rinsed with distilled water. The treated monolith was placed in 150 ml of distilled water. 10 drops of concentrated $HNO_3$ and 36 ml of a 1% strength by weight aqueous solution of hypophosphoric acid and then 20 ml of a palladium nitrate solution (1% by weight) were added. The mixture was heated first to 60° C. for 17 min and then to 80° C. for one hour. The mixture was then cooled and the catalyst monolith washed with distilled water and dried at 120° C. for 16 hours.

The reaction medium used for the preparation of hydrogen peroxide consisted of methanol with 0.4% by weight of sulfuric acid, 0.1% by weight of phosphoric acid and 6 ppm of bromide (as sodium bromide) added. The reactor was flooded with the reaction medium. A stream of 72.8 g/h of reaction medium, 48.6 l/h of oxygen and 5.5 l/h of hydrogen (gases referring to standard temperature and pressure) was then passed through the reactor. The product/gas mixture was continuously discharged at the top of the reactor.

The conversion based on hydrogen was 76% (according to a determination of the hydrogen content in the effluent gas) and the selectivity was 82%. The concentration of the resulting methanolic hydrogen peroxide solution was 7% by weight (titration with 0.1 N $KMnO_4$).

Example 3
Epoxidation of Propene with Hydrogen Peroxide Over a Fixed-bed Catalyst Flows of 27.5 g/h of hydrogen peroxide (20% by weight, obtained as in Example 1), 65 g/h of methanol and 13.7 g/h of propylene were passed through a reactor battery consisting of two reactors which had a reaction volume of 190 ml each and which were packed with 10 g of titanium silicalite-1 (TS-1) shaped into all-catalyst extrudates having a diameter of 2 mm at a reaction temperature of 40° C. and a reaction pressure of 20 bar. The reaction mixture exited from the second reactor and was depressurized to atmospheric pressure in a Sambay evaporator. The removed low boilers were analyzed on-line by gas chromatography. The liquid reaction effluent was collected, weighed and also analyzed by gas chromatography.

The hydrogen peroxide conversion decreased throughout the running time from initially 96% and reached 63% after 400 h. The selectivity, based on hydrogen peroxide, was 95%.

Example 4
Regeneration of Deactivated Catalyst

The deactivated fixed-bed catalyst of Example 3, which was covered with organic products, was rinsed with methanol and then dried at 120° C. for five hours. 56 g of the dried shaped catalyst were placed in a rotary tube. First, the rotary tube was rotated very slowly (2 rph) and heated to 500° C. at 4° C./min under nitrogen (20 l/h). A gas mixture containing 9% by volume of oxygen and 91% by volume of nitrogen was then fed into the rotary tube at 500° C. for 2 h. The volume percentage of oxygen in the gas stream was then increased to 18% by volume at 500° C. for 14 h while keeping the amount of gas constant (20 l/h). The regenerated catalyst was then cooled under a steady stream of gas. The weight loss was about 7%.

Example 5
Reuse of Regenerated Catalyst

Flows of 27.5 g/h of hydrogen peroxide (20% by weight, obtained as in Example 1), 65 g/h of methanol and 13.7 g/h of propylene were passed through a reactor battery consisting of two reactors which had a reaction volume of 190 ml each and which were packed with 10 g of the catalyst regenerated as described in Example 4 at a reaction temperature of 40° C. and a reaction pressure of 20 bar. The reaction mixture exited from the second reactor and was depressurized to atmospheric pressure in a Sambay evaporator. The separated low boilers were analyzed on-line by gas chromatography. The liquid reaction effluent was collected, weighed and also analyzed by gas chromatography.

The hydrogen peroxide conversion decreased throughout the running time from initially 96% and reached 63% after 400 h. The selectivity, based on hydrogen peroxide, was 95%.

Example 6
Dehydrogenation of Propane to Obtain Propene 210 ml of a dehydrogenation catalyst on the basis of chromium oxide/$Al_2O_3$ in the form of 2 mm extrudates were placed in a double-jacketed tube reactor (length 50 cm, internal diameter 35 mm). The reactor was heated to a wall temperature of 550° C. by means of a salt bath heat-transfer medium. Propane was passed over the reactor admixed with nitrogen (volume ratio 20:80) from a steel cylinder at a controlled pressure of 1.5 bar (LHSV=0.15/h). The effluent reaction mixture consisting of propane, propene and hydrogen was cooled to 30–40° C. and liquefied by compressing to about 35 bar to separate the $C_3$ products from the hydrogen. This liquid gas mixture was usable in the epoxidation without further purification, since only the propylene was reacted there and the propane was sufficiently inert.

Following epoxidation, unconverted $C_3$-propane/propene mixture was depressurized after testing for absence of peroxide and recycled into the reactor for propane dehydrogenation.

After a reaction time of 3 h, the conversion of propane per pass was typically about 35%, the propene selectivity being 83 mol % (GC analysis upstream of the compressor).

The deactivated catalyst was re-regenerable by adding air to the nitrogen carrier gas (max. 2% by volume of oxygen) after closing the propane feed line.

Example 7
Direct Synthesis of Hydrogenperoxide in Water

The same catalyst as in Example 4 was used. The reaction medium consisted of water to which 0.4% by weight sulphuric acid, 0.1% by weight phosphoric acid and 6 ppm bromide (in the form of sodium bromide) were added. The reaction parameters were as follows: 268.0 g/h reaction medium, 291.6 l/h oxygen, 32.4 l/h hydrogen, T=42° C. The conversion based on hydrogen was obtained by a determination of the hydrogen content of the spent gas and was 43% with a selectivity of 70%. The concentration of the obtained hydrogen peroxide solution was 5.6% by weight.

We claim:

1. A process for oxidizing an organic compound having at least one C—C double bond or a mixture of two or more thereof, comprising:

(I) preparing a hydroperoxide, (II) reacting an organic compound having at least one C—C double bond or a mixture of two or more thereof with the hydroperoxide from (I) in the presence of a zeolite catalyst, (III) regenerating the at least partially deactivated zeolite catalyst used in (II), wherein the regeneration comprises at least the following steps in sequence comprising at least two stages:

(a) heating the catalyst in a stream of inert gas to a temperature of at least 200° C., (b) subsequently, adding oxygen or an oxygen-supplying substance, wherein the amount of oxygen or oxygen-supplying substance added to the inert gas is regulated in such a manner that the temperature during regeneration does not exceed about 800° C. and does not fall below about 400° C., and (IV) conducting the reaction of (II) using a zeolite catalyst containing the catalyst regenerated in (III).

2. A process as claimed in claim 1, wherein the organic compound having at least one C—C double bond is selected from the group consisting of a linear or branched aliphatic olefin, a linear or branched aromatic olefin, a linear or branched cycloaliphatic olefin, each having up to 30 carbon atoms, and a mixture of two or more thereof.

3. A process as claimed in claim 2, wherein the olefin is obtained by dehydrogenating the corresponding saturated organic compound to obtain the olefin and hydrogen.

4. The process as claimed in claim 3, wherein the dehydrogenation is conducted in the presence of a heterogeneous catalyst containing at least one of the following elements:

Sc, Y, La, Ti, Zr, Hf, V, Nb, Ta, Cr, Mo, W, Mn, Re, Fe, Ru, Os, Co, Rh, Ir, Ni, Pd, Pt, Cu, Ag, Au, B, Al, Ga, C, Si, Ge and Sn.

5. A process as claimed in claim 1, wherein the zeolite catalyst has micropores, mesopores, macropores, micro- and mesopores, micro- and macropores or micro-, meso- and macropores.

6. A process as claimed in claim 1, wherein the zeolite catalyst used is a catalyst obtainable by a process which comprises:

(i) adding to a mixture comprising a zeolite or a mixture of two or more thereof a mixture comprising at least one alcohol and water, and (ii) kneading, shaping, drying and calcining of the mixture from (i).

7. A process as claimed in claim 1, wherein the at least partially deactivated zeolite catalyst of step (III) is regenerated by a process comprising:

(a) heating of an at least partially deactivated catalyst to 250° C.–600° C. in an atmosphere containing less than 2% by volume of oxygen, and (b) subjecting the catalyst to a gas stream containing an oxygen-generating substance or oxygen or a mixture of two or more thereof in an amount in the range from 0.1 to 4% by volume at from 250 to 800° C.

8. A process as claimed in claim 7, wherein, in step (b), said temperature ranges from 350 to 600° C.

9. A process as claimed in claim 1, wherein the regeneration of (III) of the at least partially deactivated catalyst is carried out in an apparatus for conducting the reaction of (II) without removing the zeolite catalyst from the apparatus.

10. The process as claimed in claim 1, wherein the zeolite catalyst is selected from the group consisting of a titanium, zirconium, vanadium, chromium and niobium containing zeolites each having a pentasil structure established by X-ray assignment to a MFI, BEA, MOR, TON, MTW, FER, CHA, ERI, RHO, GIS, BOG, NON, EMT, HEU, KFI, FAU, DDR, MTT, RUT, LTL, MAZ, GME, NES, OFF, SGT, EUO, MFS, MCM-22, MEL, or a MFI/MEL mixed structure or a mixture of at least two of said zeolites.

11. A process as claimed in claim 1, the oxygen content of the gas in stage (b) ranges from more than 5% to less than 50%.

* * * * *